United States Patent [19]

Morozov et al.

[11] Patent Number: 5,070,076

[45] Date of Patent: Dec. 3, 1991

[54] THYMUS-GLAND PREPARATION AND METHOD FOR PRODUCING SAME

[75] Inventors: Vyacheslav G. Morozov; Vladimir K. Khavinson, both of Leningrad, U.S.S.R.

[73] Assignee: Leningradsky Gosudarstvenny Pedagogichesky Institut, Moscow, U.S.S.R.

[21] Appl. No.: 437,283

[22] Filed: Nov. 15, 1989

Related U.S. Application Data

[63] Continuation of Ser. No. 117,675, Nov. 5, 1987, abandoned, which is a continuation-in-part of Ser. No. 777,006, Sep. 17, 1985, abandoned, which is a continuation of Ser. No. 618,958, Jun. 11, 1984, abandoned.

[51] Int. Cl.$^5$ ............... A61K 37/02; C07K 15/06; C07K 3/02
[52] U.S. Cl. .................... 514/21; 424/580; 530/837
[58] Field of Search ............. 424/580; 530/837; 514/21

[56] References Cited

U.S. PATENT DOCUMENTS 4,374,828  2/1983  Folkers et al. ............... 530/837

FOREIGN PATENT DOCUMENTS 48-11930  4/1973  Japan ............... 424/95

OTHER PUBLICATIONS

Dardenne et al., Chem. Abstracts, vol. 97:175845j (1982).

*Primary Examiner*—Jacqueline Stone
*Attorney, Agent, or Firm*—Burgess, Ryan & Wayne

[57] ABSTRACT

A thymus-gland preparation is provided which contains polypeptides with a molecular weight of 600–6,000 Dalton and has the following composition, in percent by weight:

| | |
|---|---|
| polypeptides with an isoelectric point of 3.5–6.7 | 80–90 |
| polypeptides with an isoelectric point of 7–9 and a molecular weight of 2,000–4,000 Dt | 20–10. |

A method for the production of the thymus-gland preparation is also provided and comprises homogenization of thymus tissue, extraction of the resulting homogenizate with a 1–10% aqueous solution of acetic acid in the presence of zinc chloride for at least 24 hours, separation of the resulting extract into a precipitate and a supernatant liquid which is treated with an organic solvent, followed by isolation of the desired product.

14 Claims, No Drawings

THYMUS-GLAND PREPARATION AND METHOD FOR PRODUCING SAME

RELATED APPLICATION

This application is a continuation of application Ser. No. 117,675, filed Nov. 5, 1987, now abandoned, which is a continuation-in-part of U.S. patent application Ser. No. 777,006, filed Sept. 17, 1985, abandoned, which is a continuation of U.S. patent application Ser. No. 618,958, filed June 11, 1984, now abandoned, both applications are incorporated herein by reference.

FIELD OF THE INVENTION

The present invention relates to medicine and, more specifically, to a thymus-gland preparation and a process for producing same and is useful for restoring disturbed processes of immunogenesis, regeneration, homopoiesis, hemocoagulation and normalization of carbohydrate, fat and protein metabolism in human beings.

BACKGROUND OF THE INVENTION

It is known that in extracts of thymus-gland tissues of humam beings and animals physiologically-active substances are present which provide a marked influence on the organism's growth and development, as well as on some immunological and metabolic processes (cf. Comsa, T., Amer. J. Med. Sci. 250, 79, 1965; Goldstein A. et al., J. Immunol., 140, 359, 1970; USSR Inventor's Certificate No. 459227, U.S. Pat. No. 4,120,951).

According to the data available from the literature, an extract from calf's thymus-gland (thymosin) is used for therapeutic purposes for the recovery of the function of the immunity system in human beings in the case of certain oncological and congenital immunodeficiency diseases (Goldstein A. et al., Transplant Proc. 7, 1 (Supp. 1), 681, 1975; Sakai et al, Cancer 36,3,973, 1975).

The administration of the thymus preparation to patients resulted in the recovery of disturbed immunological response of the organism Nevertheless, up till now the therapeutical efficiency of physiologically active substances obtained from the thymus-gland tissue and indications of their use in the medical practice have been studied but insufficiently.

Known in the art is a medicinal preparation from thymus-gland tissue—thymosin (cf. Goldstein A. et al., Proc. Nat. Acad. Sci., USA, 69, 7, 1800, 1972) which comprises a complex (about 30 components) of acid polypeptides with a molecular weight of 1,000 to 14,000 Dt (Hooper et al., Ann. N.Y. Acad: Sci., 249, 125, 1975). For the preparation of thymosin the following procedure is used (Hooper at al., 1975).

Calf's thymus is homogenized in a 0.15 M solution of NaCl, centrifuged at 14,000 g, the supernatant liquid is isolated and subjected to heating at the temperature of 80° C., the formed precipitate is removed by filtration, while the remaining solution is added with 5 volumes of acetone. The resulting precipitate is dried on the filter, then again dissolved and salted out with ammonium sulphate first at a 25% saturation and then at a 50% saturation. The precipitate resulting from the salting-out operation is filtered, desalted in a column with Sephadex G-25 and lyophilized. At this stage of purification the obtained complex of polypeptides contained in the preparation has a most clearly pronounced biological activity—ability for stimulation of cell immunity (Hooper et al., 1975).

Further purification of the preparation causes reduction of its biological activity.

Thymosin produced by this method contains a complex of acid polypeptides with an isoelectric point of 3.5–6.7 and a molecular weight of 1,000–14,000 Dt with a substantial predominance of aspartic acid and glutamic acid amounting in total to 50% by weight of thymosin.

It should be noted, however, that this method for the preparation of thymosin is rather complicated and multi-staged (10 stages altogether). A number of operations are associated with certain difficulties in application of this process in industry (ultracentrifugation, the use of Sephadex packing). This method fails to provide a high yield of the medicinal preparation-thymosin. Thymosin also causes, in a number of patients, some side effects and allergic responses. The therapeutical efficiency of thymosin and possibilities for its application in medical practice have not been sufficiently studied.

It is an object of the present invention to provide a thymus-based medicinal preparation incorporating alkaline polypeptides and possessing a broad spectrum of the pharmacological action, while eliminating side effects and allergic responses upon its administration.

It is another object of the present invention to provide a method for producing a medicinal preparation from thymus which would ensure a high yield thereof by a simple process enabling isolation of alkaline polypeptides ensuring a high clinical efficiency in immunodeficient cases.

SUMMARY OF THE INVENTION

These objects are accomplished by the providing a thymus-based preparation comprising polypeptides with an isoelectric point of 3.5–6.7 which, according to the present invention, contains polypeptides with a molecular weight of 600 to 6,000 Dt out of which 10 to 20% by weight have an isoelectric point of 7–9 and a molecular weight of 2,000 to 4,000 Dt.

DETAILED DESCRIPTION OF THE INVENTION

The use of the thymus-gland preparation according to the present invention in medical practice makes it possible to stimulate a reduced immunological reactivity of the organism, and to enhance the activity of reparative processes and hemopoiesis. The use of the thymus-gland preparation according to the present invention in hospitals will make it possible to considerably reduce the duration of treatment of patients with chronical diseases and disturbed regeneration processes, which may become a decisive factor in relation to the effectiveness of the use of the present invention in medicine.

The thymus-gland preparation according to the present invention, owing to the presence of alkaline polypeptides therein, stimulates processes of regeneration of injured tissues, unlike the known thymus-based preparations, which is manifested in a reduced duration of healing of wounds, ulcers and in stimulation of hemopoiesis of increasing the number of leuccocytes, thrombocytes and erythrocytes in the case of a reduced content thereof in peripheral blood.

The thymus-gland preparation according to the present invention does not cause any side effects or allergic responses, whereas from the literature it is known that the administration of thymosin causes allergic responses in 20-30% of patients.

The present invention relates also to a method for producing a thymus-gland preparation comprising homogenization of thymus tissue, separation of the resulting homogenizate into a precipitate and a supernatant liquid, treatment of the latter with an organic solvent, followed by isolation of the desired product, wherein, according to the present invention, prior to the separation the homogenizate of the tissue of thymus-gland is extracted with a 1-10% aqueous solution of acetic acid in the presence of zinc chloride for a period of at least 24 hours.

The method according to the present invention features a simple procedure and is readily reproducible on a commercial scale. The method enables hydrolysis of large-size proteins and other high-molecular compounds, a sufficiently high yield of the preparation from thymus-gland at a high degree of purification; this preparation, when introduced into a human organism, does not cause side effects or allergic responses.

The use of a rather long-time extraction with acetic acid in the presence of catalytical amounts of zinc chloride contributes to the recovery of polypeptides of the alkaline nature which, while being present in the preparation, ensure an enlarged scope of its pharmacological effect.

It is advisable, with the view to ensuring a maximum recovery of polypeptides with an isoelectric point of 7-9 and a molecular mass of 2,000 to 4,000 Dt possessing a maximum biological activity, to carry out the extraction for a period of 48 to 72 hours at a pH of 2.5 to 4 and at a temperature within the range of from 5° to 15° C. in the presence of zinc chloride in an amount of 0.2 to 2 g per liter of acetic acid.

It is preferred, for a fuller recovery of biologically active substances-alkaline polypeptides and conservation of the starting materials, to keep the tissue of thymus-gland at a temperature of −30° to −50° C. for at least 100 hours prior to homogenization.

DETAILED DESCRIPTION OF THE INVENTION

We have studied the properties of the preparation from thymus-gland by the method of ion-exchange chromatography on a carboxyl cationite "Blocarb" in the H+ form (cf. N. N. Kuznetsova et al., High-molecular Comp., 18a, 2, 235, 1976), gel-filtration (Fish et al., T. Biol. Chem., 244, 4989, 1969), zonal electrophoreasis on paper and in a polyacrylamide gel (following conventional procedures) and aminoacid analysis (by the Stein and Moore method, T. Biol. Chem., 176, 307, 1948). By the method of ion-exchange chromatography it has been found that the recovered compounds contained 3 fractions in a particular percentage ratio differing in their electrochemical properties.

The physicochemical characteristics of the fractions contained in the preparation of thymus-gland according to the present invention are given in Table 1 hereinbelow.

TABLE 1

| Component | Content, weight % | Molecular weight, Dt | Isoelectric point, pH units |
|---|---|---|---|
| Fraction I | 40-70 | 600-1,000 | 3.5-5.0 |
| Fraction II | 20-40 | 5,000-6,000 | 5.5-6.7 |
| Fraction III | 10-20 | 2,000-4,000 | 7.0-9.0 |

Fractions, I, II and III comprise a number of components identified by the method of zone electrophoresis. The molecular weight of each fraction was determined by means of the gel-filtration method using Sephadex G-25.

For the determination of the aminoacid composition of peptides of the above-mentioned fractions an automatic amino acid analyzer "LKB-3201" (Sweden) was used; the determination procedure was as described by Spackman D. H. et al., Anal. Chem., 1958, 30, 1190-1206.

The aminoacid composition of the thymus-gland preparation according the present invention is given in Table 2.

| Aminoacid | Content of aminoacid in the preparation of this invention, mol. % | Content of fractions, mol. % | | |
|---|---|---|---|---|
| | | Fraction I | Fraction II | Fraction III |
| 1 | 2 | 3 | 4 | 5 |
| Aspartic acid | 5.8 | 6.3 | 0.6 | 4.2 |
| Threonine | 5.7 | 6.3 | 6.4 | 5.8 |
| Serine | 5.7 | 6.5 | 7.5 | 10.4 |
| Glutamic acid | 6.2 | 8.6 | 14.1 | 6.2 |
| Proline | 10.1 | 10.8 | 13.2 | 9.5 |
| Glycine | 8.6 | 10.4 | 11.7 | 10.1 |
| Alanine | 10.7 | 12.6 | 8.7 | 18.6 |
| Cystine | 3.4 | 2.6 | 1.0 | 0.9 |
| Valine | 8.8 | 5.2 | 6.5 | 3.5 |
| Methionine | traces | traces | — | — |
| Isoleucine | 3.9 | 2.3 | 4.9 | 1.3 |
| Leucine | 6.7 | 6.2 | 5.8 | 3.2 |
| Tyrosine | 2.4 | 1.2 | 2.4 | 0.8 |
| Phenylalanine | 3.2 | 1.7 | 3.3 | 0.9 |
| Histidine | 2.9 | 2.9 | 2.2 | 0.5 |
| Lysine | 7.0 | 8.5 | 7.1 | 21.6 |

The biological activity and a broad range of the pharmacological effect of the preparation from thymus-gland according to the present invention with a molecular weight of 600 to 6,000 Dt are associated with the presence therein of 10-20% by weight of polypeptides with an iso-electric point of 7-9 and a molecular weight of 2,000 to 4,000 Dt characterized by the presence of basic aminoacid moieties, for example, lysine. As regards its physicochemical properties and aminoacid composition, the thymus-gland preparation according to the present invention substantially differs from thymosin which consists of a complex of acid polypeptides (isoelectric point of 3.5-6.7) with a molecular weight of from 1,000 to 14,000 Dt and a considerable predomination of aspartic and glutamic acids amounting in total to 50% by weight of the preparation (Hooper et al., Ann. N.Y. Acad. Sci., 249, 125, 1975).

The thymus-gland tissue which is employed in the present invention can be obtained from several mammals including calves, sheep, pigs, horses and the like. In practice, calves are a common source of the thymus tissue.

The thymus-gland preparation according to the present invention is produced in the following manner.

The thymus tissue, such as that obtained from a calf, is cleaned to remove vessels, blood clots, fatty tissues, washed with water and homogenized.

In order to ensure conservation of the starting material and increase yield of biologically active substances—polypeptides with isoelectric points of 3.5-6.7 and 7-9, it is advisable that prior to the homogenation the thymus tissue be maintained at a temperature within the range of from −50° to −30° C. or be treated with an organic solvent such as acetone, chloroform, ethanol at a temperature of from −20° to −1° C.

The thymus tissue homogenizate is extracted with a 1-10% aqueous solution of acetic acid in the presence of zinc chloride for at least 24 hours. Extraction under these conditions contributes to a fullest recovery of polypeptides with a molecular mass of 2,000 to 4,000 Dt and an isolectric point of 7-9 and ensures elimination of proteins and high molecular weight compounds causing allergic responses upon administration of the thymus-gland preparation to patients. Optimal conditions for the extraction are the following: pH=2.5-4, temperature, 5-15° C. and duration, 48-72 hours at a content of zinc chloride of 0.2 to 2 g per liter of acetic acid.

On completion of the extraction the resulting substrate is separated into a precipitate and a supernatant liquid which is treated with an organic solvent such as acetone, chloroform, ethanol, followed by the recovery of the formed precipitate. The latter is dried to the powder-like state which powder contains biologically active substances—polypeptides.

The powder is dissolved in acetic acid, the solution is sterilized by filtration and poured into 1 ml sterile flasks which are then closed with rubber stoppers One flask contains 10 mg. of substances recovered from thymus.

The thus-obtained thymus-gland preparation according to the present invention contains biologically-active substances—polypeptides having a molecular weight of 600 to 6,000 Dt with the following proportions in weight per cent:

| | |
|---|---|
| Polypeptides with an isoelectric point of 3.5-6.7 | 90-80 |
| Polypeptides with an isoelectric point of 7-9 | 10-20 |

The thymus-gland preparation according to the present invention comprises a powder having a white color or a white color with a yellowish tint powder soluble in a 5% solution of acetic acid, soluble in water, substantially insoluble in an alcohol; it contains substantially no protein; pH of a 1% aqueous solution is 5-5.8. The thymus preparation is stored in a dry light-protected place at a temperature of not more than +20° C. for two years.

The thymus-gland preparation can be indicated for the treatment of acute pyo-inflammatory diseases of bones and soft tissues, chronical post-traumatic and hematogenous osteomyelitis, bone fractures, burning lesions, trophic ulcers, decubitus, radial necrosis of tissues, obliterating aterosclersis, chronic pheumonia, stomach and duodenum ulcer disease; conditions connected with hypofunction of thymus, inhibition of immunity and hemopoiesis after radiotherapy and chemotheraphy in oncological patients. The thymus-gland preparation according to the present invention can be indicated also for the purpose of prophylaxis of infectional complications, inhibition of immunity, hemopoiesis, regeneration process during the post-traumatic and post-operation periods, in the course of radiotherapy or chemotherapy, with the use of high doses of antibiotics. It can be also used in the case of intolerance towards antibacterial therapy or absence of any effect therefrom as well as a normalizing agent at functional disturbances of carbohydrate, fat and protein metabolism in the organism.

We have suggested a simple and inexpensive process for the production of the thymus-gland preparation according to the present invention which process can be readily implemented on a commercial scale to give a high-quality preparation in a high yield exceeding the yield of, for example, thymosin by 5 times.

For a better understanding of the present invention, some specific examples illustrating the production of the thymus-gland preparation are given hereinbelow.

EXAMPLE 1

Thymus-gland tissue obtained from calves in the amount of 500 g is cleaned from vessels, blood clots, fatty tissues, then washed with water and acetone, whereafter it is kept in acetone taken in the weight ratio of 4:1 to the thymus tissue at the temperature of −1° C. for 24 hours and subjected to homogenization. The resulting homogenizate of the thymus tissue is placed into a 3% aqueous solution of acetic acid at the weight ration therebetween of 1:6 respectively. The extraction is conducted at pH=3.2, temperature of 10° C. for 72 hours in the presence of zinc chloride taken in the amount of 1 g per liter of acetic acid. On completion of the extraction the substrate is centrifuged at 3,000 r.p.m. for 20 minutes, the supernatant liquid is separated and added with acetone at the weight ratio therebetween of 1:5 respectively. The formed precipitate is recovered by filtration and washed with acetone, then dried on the filter. The white powder obtained in the amount of 5 g contains biologically-active substances—polypetides with a molecular mass of 600 to 6,000 Dt at the following proportions thereof, per cent by mass:

| | |
|---|---|
| polypeptides with an isoelectric point of 3.5-7.7 | 80 |
| polypeptides with an isoelectric point of 7-9 | 20 |

The thus-obtained preparation from thymus-gland comprises a white powder soluble in a 5% acetic acid, water; pH of a 1% aqueous solution is 5.5.

For the production of a pharmaceutical form of the thymus-gland preparation according to the present invention, the powder produced as above is dissolved in 500 ml of a 1% acetic acid. The solution of the preparation is sterilized by filtration and poured into 1 ml sterile flasks, lyophilized and closed with rubber stoppers. As a result, one flask contains 10 mg of substances recovered from the thymus tissue.

EXAMPLE 2

A thymus tissue obtained from sheep in the amount of 500 g is cleaned to remove vessels, blood clots, fatty tissues, washed with water and chloroform and then kept in chloroform taken in the weight ratio to the thymus tissue of 8:1 at the temperature of −10° C. for 48 hours, whereafter it is subjected to homogenization. The resulting homogenizate of the thymus tissue is placed into a 1% aqueous solution of acetic acid at their weight ratio of 1:10 respectively. The extraction is conducted at pH=4, temperature of 15° C. for 48 hours in the presence of zinc chloride taken at the rate of 2 g per liter of acetic acid. On completion of the extraction the substrate is subjected to filtration for 24 hours, the supernatant liquid is separated and added with chloroform in the weight ratio therebetween of 1:8 respectively. The formed precipitate is recovered by filtration and washed with chloroform, then dried on the filter. The thus-obtained white powder in the amount of 3 g contains biologically-active substances—polypeptides with a molecular mass of 600 to 6,000 Dt at the following ratio thereof, per cent by mass:

| polypeptides with an isoelectric point of 3.5–6.7 | 90 |
| polypeptides with an isoelectric point of 7–9 | 10. |

The resulting preparation of thymus-gland tissue comprises a white powder soluble in a 5% acetic acid and water; pH of a 1% aqueous solution is 5.8.

The solution of the preparation is sterilized by filtration and poured into 1 ml sterile flasks, then lyophilized and closed with rubber stoppers. As a result, one flask contains 10 mg of the substances recovered from the thymus tissue.

EXAMPLE 3

A thymus tissue obtained from pigs in the amount of 500 g is cleaned rom vessels, blood clots, fatty tissues, washed with water and subjected to homogenization. The resulting homogenizate of the thymus tissue is placed into a 10% aqueous solution of acetic acid at their weight ratio of 1:4 respectively. The extraction is conducted at the pH=2.5, temperature of 5° C for 24 hours in the presence of zinc chloride taken at the rate of 0.2 g per liter of acetic acid. On completion of the extraction the substrate is centrifuged at 5,000 r.p.m. for 10 minutes, the supernatant liquid is separated and ethanol is added thereto at the weight ratio therebetween of 1:10 respectively. The formed precipitate is separated by filtration and washed with ethanol, then dried on the filter. The thus-obtained white powder in the amount of 4 g contains biologically-active substances—polypeptides with a molecular weight of 600 to 6,000 Dt at the following proportions thereof (per cent by weight):

| polypeptides with an isoelectric point of 3.5–6.7 | 87 |
| polypeptides with an isoelectric point of 7–9 | 13. |

The thus-produced thymus-gland preparation comprises a white powder soluble in a 5% acetic acid; pH of a 1% aqueous solution is 5.3.

To produce a pharmaceutical form of the thymus-gland preparation, the powder is dissolved in 400 ml of a 3% acetic acid. The solution of the preparation is sterilized by filtration and poured into 1 ml sterile flasks, then lyophilized and closed with rubber stoppers As a result, one flask contains 10 mg of the substances recovered from the tissue of thymus-gland.

EXAMPLE 4

Thymus tissue obtained from horses in the amount of 500 g is cleaned to remove vessels, blood clots, fatty tissues, washed with water, kept at the temperature of −30° C. for 200 hours, whereafter it is subjected to homogenization. The resulting homogenizate of the thymus tissue is placed into a 5% aqueous solution of aqueous solution of acetic acid at their weight ratio of 1:5 respectively. The extraction is conducted at pH=4, temperature of 12° C. for 56 hours in the presence of zinc chloride taken at the rate of 0.5 g per liter of acetic acid. On completion of the extraction the substrate is centrifuged for 20 minutes at 4,000 r.p.m., the supernatant liquid is separated and acetone is added thereto in the weight ratio therebetween of 1:6 respectively. The formed precipitate is separated by centrifugation and washed with acetone, dried on the filter. The resulting white powder with a yellowish tint in the amount of 5.5 g contains biologically-active substances—polypeptides with a molecular weight of 600 to 6,000 Dt at the follow proportions thereof (per cent by weight):

| polypeptides with an isoelectric point of 3.5–6.7 | 82 |
| polypeptides with an isoelectric point of 7–9 | 18. |

The produced preparation from thymus-gland comprises a white powder with a yellowish tint, it is soluble in a 5% acetic acid; pH of a 1% aqueous solution is 5.2.

To produce a pharmaceutical form of the thymus-gland preparation, the resulting powder is dissolved in 550 ml of a 4% acetic acid. The solution of the preparation is sterilized by filtration and poured into 1 ml sterile flasks, then lyophilized and closed with rubber stoppers. As a result, one flask contains 10 mg of the substances recovered from the thymus tissue.

EXAMPLE 5

Thymus tissue obtained from calves in the amount of 500 g is cleaned to remove vessels, blood clots, fatty tissues, washed with water, kept at the temperature of −50° C. for 100 hours, whereafter it is subjected to homogenization. The resulting homogenizate of the thymus tissue is placed into a 2% aqueous solution of acetic acid at their weight ratio of 1:7 respectively. The extraction is conducted at pH=3.0, temperature of 8° C. for 60° C. in the presence of zinc chloride taken in the amount of 1.5 g per liter of acetic acid. On completion of the extraction the substrate is centrifuged at 6,000 r.p.m. for 10 minutes, the supernatant liquid is separated and ethanol is added thereto at their weight ratio of 1:10 respectively. The formed residue is recovered by filtration and washed with ethanol, then dried on the filter. The resulting white powder in the amount of 5.6 g contains biologically-active substances—polypeptides with a molecular weight of 600 to 6,000 Dt at the following proportions thereof, per cent by weight

| polypeptides with an isoelectric point of 3.5–6.7 | 80 |
| polypeptides with an isoelectric point of 7–9 | 20. |

The resulting white powder is soluble in a 5% acetic acid, water; pH of a 1% aqueous solution is 5.4.

To produce a pharmaceutical form of the thymus-gland preparation, the powder produced as above is dissolved in 570 ml of a 2% acetic acid. The solution of the preparation is sterilized by filtration and poured into 1 ml sterile flasks, then lyophilized and closed with rubber stoppers. As a result, one flask contains 10 mg of the substances recovered from the thymus tissue.

What is claimed is:

1. A method for producing a thymus-gland preparation containing polypeptides with a molecular weight of 600 to 6,000 Dt having the following composition:
   80-90 percent by weight of polypeptides with an isoelectric point of 3.5-6.7; and
   20-10 percent by weight of polypeptides with an isoelectric point of 7-9 and molecular weight of 4,000-6,000 Dt, said method comprising:
   homogenizing thymus tissue;
   extracting the resulting homogenizate with a 1-10% aqueous solution of acetic acid in the presence of zinc chloride, said zinc chloride being present in an amount of 0.2-2 g per liter of said solution of acetic acid;
   separating the resulting extract into a precipitate and supernatant liquid;
   treating the supernatant liquid with an organic solvent to form a precipitate; and
   recovering said thymus-gland preparation.

2. A method as claimed in claim 1, wherein the extraction is conducted at a pH of 2.5-4 and temperature of 5°-15° C.

3. A method as claimed in claim 1 wherein prior to said homogenization, the thymus tissue is kept at a temperature of from −50° C. to −30° C. for a period of from 24 to 100 hours.

4. A method as claimed in claim 1 comprising:
   homogenizing thymus tissue;
   extracting the resulting homogenizate with 1-10% aqueous solution of acetic acid containing from 0.2 to 2 g of zinc chloride per liter of said solution of acetic acid for at least 24 hours;
   separating the resulting extract into a precipitate and supernatant liquid;
   treating the supernatant liquid with an organic solvent selected from the group consisting of acetone, chloroform or ethanol to form a precipitate; and
   recovering the desired thymus gland preparation.

5. The method of claim 4 wherein the organic solvent is acetone.

6. The method of claim 4 wherein the organic solvent is chloroform.

7. The method of claim 4 wherein the organic solvent is ethanol.

8. The thymus gland preparation produced by the process of claim 1.

9. A thymus gland preparation having the following physicochemical characteristics.

| Component | Content, Mass % | Molecular Mass, Dt | Isoelectric Point, pH Units |
|---|---|---|---|
| Fraction I | 40-70 | 600-1,000 | 3.5-5.0 |
| Fraction II | 20-40 | 5,000-6,000 | 5.5-6.7 |
| Fraction III | 10-20 | 2,000-4,000 | 7.0-9.0 | and the aminoacid composition:

| Aminoacid | Aminoacid Content Mol. % | Fraction I | Fraction II | Fraction III |
|---|---|---|---|---|
| Aspartic Acid | 5.8 | 6.3 | 0.6 | 4.2 |
| Threonine | 5.7 | 6.3 | 6.4 | 5.8 |
| Serine | 5.7 | 6.5 | 7.5 | 10.4 |
| Glutamic Acid | 6.2 | 8.6 | 14.1 | 6.2 |
| Proline | 10.1 | 10.8 | 13.2 | 9.5 |
| Glycine | 8.6 | 10.4 | 11.7 | 10.1 |
| Alanine | 10.7 | 12.6 | 8.7 | 18.6 |
| Cystine | 3.4 | 2.6 | 1.0 | 0.9 |
| Valine | 8.8 | 5.2 | 6.5 | 3.5 |
| Methionine | traces | traces | — | — |
| Isoleucine | 3.9 | 2.3 | 4.9 | 1.3 |
| Leucine | 6.7 | 6.2 | 5.8 | 3.2 |
| Tyrocine | 2.4 | 1.2 | 2.4 | 0.8 |
| Phenylalanine | 3.2 | 1.7 | 3.3 | 0.9 |
| Histidine | 2.9 | 2.9 | 2.2 | 0.5 |
| Lysine | 7.0 | 8.5 | 7.1 | 21.6 |
| Arginine | 8.5 | 7.8 | 4.6 | 2.1 |
| Tryptophan | traces | traces | traces | traces |

10. A method for producing a thymus-gland preparation containing polypeptides with a molecular weight of 600 to 6,000 Dt having the following composition:
   80-90 percent by weight of polypeptides with an isoelectric point of 3.5-6.7; and
   20-10 percent by weight of polypeptides with an isoelectric point of 7-9 and molecular weight of 4,000-6,000 Dt, said method comprising:
   maintaining thymus tissue at a temperature of from −50° C. to −30° C. for a period of from 24 to 100 hours;
   homogenizing said thymus tissue;
   extracting the resulting homogenizate with 1-10% aqueous solution of acetic acid containing from 0.2 to 2 g of zinc chloride per liter of said solution of acetic acid for at least 24 hours and wherein the extraction is conducted at a pH of 2.5-4 and temperature of 5°-15° C.;
   separating the resulting extract into a precipitate and supernatant liquid;
   treating the supernatant liquid with an organic solvent selected from the group consisting of acetone, chloroform or ethanol to form a precipitate; and
   recovering the desired thymus gland preparation.

11. A method for producing a thymus-gland preparation which produces essentially no side effects or allergic reactions, and wherein said preparation contains polypeptides with a molecular weight of 600 to 6,000 Dt having the following composition:
   80-90 percent by weight of polypeptides with an isolectric point of 3.5-6.7;
   20-10 percent by weight of polypeptides with an isoelectric point of 7-9 and molecular weight of 4,000-6,000 Dt, and wherein aspartic and glutamic are not the predominant amino acids, said method comprising:
   homogenizing thymus tissue;
   extracting the resulting homogenizate with a 1-10% aqueous solution of acetic acid in the presence of zinc chloride, said zinc chloride being present in an amount of 0.02-2 g per liter of said solution of acetic acid;
   separation the resulting extract into a precipitate and supernatant liquid;
   treating the supernatant liquid with an organic solvent to form a precipitate; and
   recovering said thymus-gland preparation.

12. A thymus-gland preparation containing polypeptides with a molecular weight of 600 to 6,000 Dt and having the following composition:
   80-90 percent by weight of polypeptides with an isoelectric point of 3.5-6.7; and
   20-10 percent by weight of polypeptides with an isoelectric point of 7-9 and molecular weight of 2,000-4,000 Dt.

13. A pharmaceutical preparation comprised of the thymus-gland preparation of claim 12 and a pharmaceutically acceptable carrier.

14. A method for stimulating immunological activity and enhancing reparative processes and hemopoiesis in a patient which comprises administering to said patient an effective amount of the pharmaceutical composition of claim 13.

* * * * *